United States Patent
Narisawa et al.

(10) Patent No.: US 9,771,313 B2
(45) Date of Patent: Sep. 26, 2017

(54) CYCLOHEXANOL, METHOD FOR PRODUCING CYCLOHEXANOL, AND METHOD FOR PRODUCING ADIPIC ACID

(75) Inventors: Naoki Narisawa, Tokyo (JP); Katsutoshi Tanaka, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 0 days.

(21) Appl. No.: 14/130,420

(22) PCT Filed: Jun. 28, 2012

(86) PCT No.: PCT/JP2012/066545
§ 371 (c)(1),
(2), (4) Date: Feb. 12, 2014

(87) PCT Pub. No.: WO2013/008637
PCT Pub. Date: Jan. 17, 2013

(65) Prior Publication Data
US 2014/0256981 A1    Sep. 11, 2014

(30) Foreign Application Priority Data
Jul. 12, 2011    (JP) .................... 2011-154023

(51) Int. Cl.
| | |
|---|---|
| C07C 51/00 | (2006.01) |
| C07C 51/31 | (2006.01) |
| C07C 29/04 | (2006.01) |
| C07C 29/80 | (2006.01) |
| C07C 35/08 | (2006.01) |

(52) U.S. Cl.
CPC .............. *C07C 51/31* (2013.01); *C07C 29/04* (2013.01); *C07C 29/80* (2013.01); *C07C 35/08* (2013.01); *C07C 51/313* (2013.01); *C07C 51/316* (2013.01); *C07C 2601/14* (2017.05)

(58) Field of Classification Search
CPC ............ C07C 29/04; C07C 7/06; C07C 51/31
See application file for complete search history.

(56) References Cited

U.S. PATENT DOCUMENTS

| | | | |
|---|---|---|---|
| 2,719,172 A | 9/1955 | Nebe et al. | |
| 4,588,846 A | 5/1986 | Mitsui et al. | |
| 6,245,907 B1 * | 6/2001 | Suh et al. | 540/534 |
| 6,552,235 B2 | 4/2003 | Takamatsu et al. | |
| 8,237,005 B2 | 8/2012 | Ban | |
| 2004/0073061 A1 | 4/2004 | Kawase et al. | |
| 2012/0095263 A1 | 4/2012 | Carvin et al. | |

FOREIGN PATENT DOCUMENTS

| | | |
|---|---|---|
| CN | 1037502 A | 11/1989 |
| CN | 1092757 A | 9/1994 |
| CN | 1487914 A | 4/2004 |
| EP | 0 614 866 B1 | 9/1994 |
| JP | 61-257940 A | 11/1986 |
| JP | 2-31056 B2 | 7/1990 |
| JP | 7-165646 A | 6/1995 |
| JP | 11-302209 A | 11/1999 |
| WO | WO 01/47845 A1 | 7/2001 |
| WO | WO 2009/031216 A1 | 3/2009 |
| WO | WO 2010/145961 A1 | 12/2010 |

OTHER PUBLICATIONS

Chen et al. Ind. Eng. Chem. Res. 2014, 53, 7079-7086.*
English translation of International Preliminary Report on Patentability and Written Opinion mailed Jan. 23, 2014, in PCT International Application No. PCT/JP2012/066545.
English translation of International Search Report mailed Oct. 2, 2012, in PCT International Application No. PCT/JP2012/066545.
Office Action Action issued Mar. 7, 2014, in Taiwanese Patent Application No. 101124826.
Extended European Search Report dated Oct. 27, 2014 for European Application No. 12811125.9.
Oppenheim et al., "Adipic Acid," Kirk-Othmer Encyclopedia of Chemical Technology, vol. 1, pp. 553-582, Mar. 14, 2003, XP055147412.

* cited by examiner

*Primary Examiner* — Clinton Brooks
*Assistant Examiner* — Ana Z Muresan
(74) *Attorney, Agent, or Firm* — Birch, Stewart, Kolasch & Birch, LLP

(57) ABSTRACT

A purified cyclohexanol of the present invention has a methylcyclopentanol concentration of 10 to 1000 ppm by weight and a cyclohexylcyclohexene isomer concentration of 15 to 500 ppm by weight. A method for producing cyclohexanol of the present invention comprises: Step 1 of producing a solution (I) containing cyclohexanol, methylcyclopentanol, and water by a hydration reaction of cyclohexene; Step 2 of separating the solution (I) into a water phase and an oil phase; Step 3 of obtaining a partially purified cyclohexanol containing methylcyclopentanol from the oil phase; and Step 4 of separating and removing methylcyclopentanol in the partially purified cyclohexanol so as to obtain a purified cyclohexanol having a methylcyclopentanol concentration of 10 to 1000 ppm by weight and a cyclohexylcyclohexene isomer concentration of 15 to 500 ppm by weight.

11 Claims, 1 Drawing Sheet

[Fig.1]
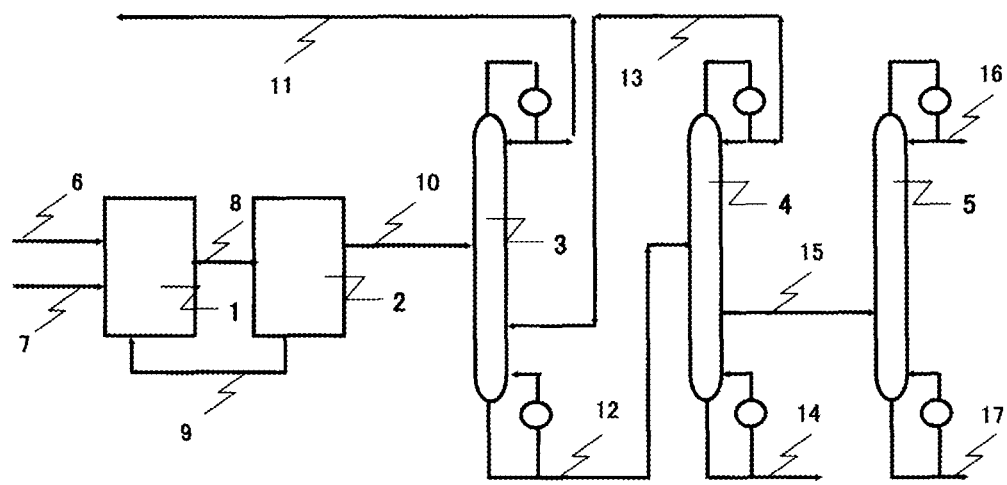
[Fig.2]
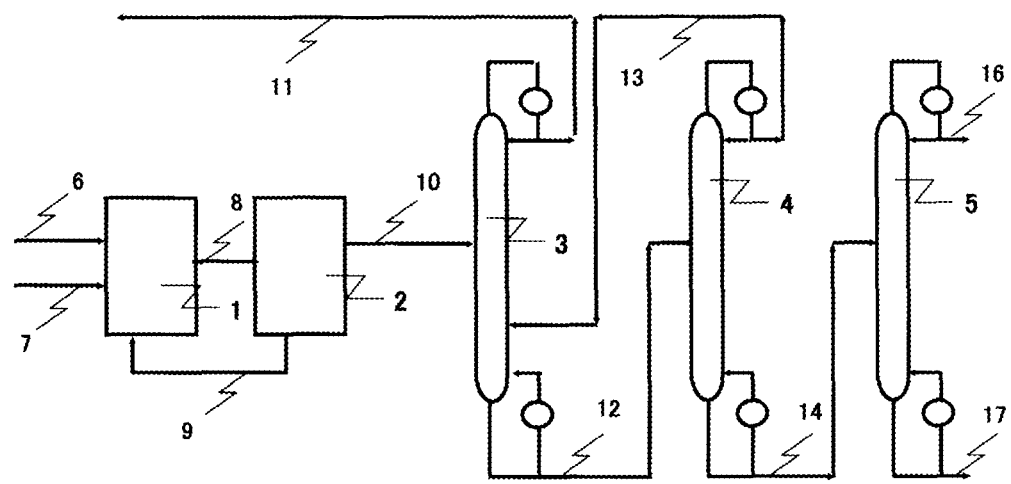

CYCLOHEXANOL, METHOD FOR PRODUCING CYCLOHEXANOL, AND METHOD FOR PRODUCING ADIPIC ACID

TECHNICAL FIELD

The present invention relates to cyclohexanol, a method for producing cyclohexanol, and a method for producing adipic acid using cyclohexanol.

BACKGROUND ART

Adipic acid is an important intermediate raw material for polyamide 66 and polyurethane. A method in which cyclohexanone and/or cyclohexanol is oxidized by nitric acid to synthesize adipic acid is industrially the mainstream as a method for producing adipic acid. A method (1) for synthesizing a ketone alcohol oil (KA oil; a mixture of cyclohexanone and cyclohexanol) by oxidization of cyclohexane, and a method (2) for synthesizing cyclohexanol by hydration of cyclohexane have been known as the method for producing cyclohexanone and/or cyclohexanol. In the production of adipic acid, a method through the method (2) for synthesizing cyclohexanol is preferable in that the method is costly advantageous as compared with a method through the method (1) for synthesizing a KA oil.

As described in Patent Document 1, a method for bringing a crystalline metallosilicate used as a solid catalyst into contact with cyclohexene in a liquid phase has been known as the method for producing cyclohexanol by hydration of cyclohexene.

LIST OF PRIOR ART DOCUMENTS

Patent Document

Patent Document 1: Japanese Patent Publication No. 2-31056

SUMMARY OF INVENTION

Problems to be Solved by Invention

The present inventors produced cyclohexanol by the hydration of cyclohexene, separated the resultant into a high-boiling point fraction and a low-boiling point fraction by distillation to obtain a purified cyclohexanol, and analyzed adipic acid obtained by nitric acid oxidation of the cyclohexanol and found, however, that the adipic acid may have a worse melting color number (an index for evaluating a degree of coloration; as the melting color number is smaller, coloration is determined to be less, and quality is higher) than that of adipic acid obtained by the method through the method (1) for synthesizing a KA oil. As a result of the investigation of the cause, the present inventors have found that cyclohexanol obtained by the hydration reaction of cyclohexene contains particular by-products inhibiting the purification of adipic acid.

Even when cyclohexanol produced from cyclohexene is purified by the method described in Patent Document 1, the obtained purified cyclohexanol is colored, which does not satisfy quality standards.

The present inventors presume that one of the causes of the coloration is based on the impossible separation of a component (high-boiling point component) having a higher boiling point than that of cyclohexanol from the purified cyclohexanol. Specifically, the present inventors presume the causes of the coloration as follows. First, in the hydration reaction of cyclohexene, the high-boiling point component may be produced by the polymerization of a raw material and/or a subject matter as by-products. In the case of an aspect of withdrawing the purified cyclohexanol from a distillation column bottom with the high-boiling point component, the high-boiling point component cannot be separated from the purified cyclohexanol. Furthermore, because the high-boiling point component may contain a substance having absorption in a visible region, the purified cyclohexanol containing the high-boiling point component is considered to be colored.

Furthermore, in the case of the aspect of withdrawing the purified cyclohexanol from the bottom together with the high-boiling point component, it inevitably takes a long time to heat cyclohexanol and the high-boiling point component at the bottom. Therefore, the possibility that cyclohexanol reacts with the high-boiling point component at the bottom to further increase the high-boiling point component cannot be denied. The purifying method for which the increase of the high-boiling point component is concerned may cause a problem in a process such as the clogging of a pipe in addition to a problem of lowering the yield of the subject matter, which is not industrially desirable.

Then, it is an object of the present invention to provide a purified cyclohexanol suitable for a raw material of adipic acid by decreasing the content of by-products inhibiting purification of adipic acid, and a method for producing adipic acid using the purified cyclohexanol.

Means for Solving Problems

Because the high-boiling point component is not distilled from the bottom together with cyclohexanol in a distillation step in the case of the purifying method for separating the high-boiling point fraction and the low-boiling point fraction from cyclohexanol, the purifying method hardly causes a problem of the increase of the high-boiling point component. However, the purifying method causes a problem of the coloration of adipic acid. As a result of diligent investigation, the present inventors have discovered that methylcyclopentanol as a by-product causes the coloration of adipic acid.

However, although the purified cyclohexanol contains methylcyclopentanol in a minute amount of about 1200 ppm by weight, the coloration of the purified cyclohexanol is observed in the case of the purifying method described in Patent Document 1. Therefore, the present inventors have considered that a further coloring causative substance exists, and continued ambitious research. As a result, the present inventors have ascertained that a substance causing the coloration is a cyclohexylcyclohexene isomer having a double bond and having absorption in a visible region among the by-products in the case of the purifying method described in Patent Document 1. Furthermore, the present inventors have discovered that for methylcyclopentanol and the cyclohexylcyclohexene isomer in cyclohexanol, there are allowable amounts for application as raw materials of adipic acid to satisfy a melting color number. In conjunction therewith, the present inventors have established a method for purifying cyclohexanol to such a level, thereby completing the present invention.

That is, the present inventors have found that adipic acid can be sufficiently purified by a method for producing adipic acid containing a step of oxidizing a purified cyclohexanol having a methylcyclopentanol concentration controlled to 10 to 1000 ppm by weight and a cyclohexylcyclohexene isomer concentration controlled to 15 to 500 ppm by weight by nitric acid, and adipic acid having no practical problem in a point of a melting color number is obtained, thereby arriving at the present invention.

That is, the present invention is as follows.

[1]

A purified cyclohexanol having a methylcyclopentanol concentration of 10 to 1000 ppm by weight and a cyclohexyl cyclohexene isomer concentration of 15 to 500 ppm by weight.

[2]

A method for producing cyclohexanol comprising:

Step 1 of producing a solution (I) containing cyclohexanol, methylcyclopentanol, and water by a hydration reaction of cyclohexene;

Step 2 of separating the solution (I) into a water phase and an oil phase;

Step 3 of obtaining a partially purified cyclohexanol containing methylcyclopentanol from the oil phase; and Step 4 of separating and removing methylcyclopentanol in the partially purified cyclohexanol so as to obtain a purified cyclohexanol having a methylcyclopentanol concentration of 10 to 1000 ppm by weight and a cyclohexyl cyclohexene isomer concentration of 15 to 500 ppm by weight.

[3]

The method for producing cyclohexanol according to [2], wherein, in the Step 3, a distillation column is used as an apparatus obtaining the partially purified cyclohexanol, and the partially purified cyclohexanol is withdrawn from a middle part of the distillation column.

[4]

The method for producing cyclohexanol according to [2] or [3], wherein, in the Step 4, a distillation column is used as an apparatus separating and removing methylcyclopentanol;

the partially purified cyclohexanol introduced into the distillation column contains 95 to 99.8% by weight of cyclohexanol and 1500 to 20000 ppm by weight of methylcyclopentanol; and temperatures of second to fifth plates from a top of the distillation column are controlled to 144 to 154° C. (700 mmHg).

[5]

A method for producing adipic acid, comprising a step of oxidizing a purified cyclohexanol having a methylcyclopentanol concentration of 10 to 1000 ppm by weight and a cyclohexyl cyclohexene isomer concentration of 15 to 500 ppm by weight by nitric acid.

Advantages of Invention

The purified cyclohexanol of the present invention is suitable as a raw material of adipic acid. The method for producing adipic acid of the present invention can suppress the production of the by-products and produce high-quality adipic acid.

BRIEF DESCRIPTION OF DRAWINGS

FIG. 1 is a schematic view showing an example of a cyclohexanol production apparatus.

FIG. 2 is a schematic view showing a cyclohexanol production apparatus used in Comparative Example 4.

MODE FOR CARRYING OUT INVENTION

Hereinafter, the embodiments of the present invention (hereinafter, referred to as "the present embodiment") will be described in detail.

It is to be noted that the present invention is not limited to the following embodiment, and that various modifications can be made within the range of the gist thereof.

<<Purified Cyclohexanol>>

A purified cyclohexanol of the present embodiment has a methylcyclopentanol concentration of 10 to 1000 ppm by weight, and preferably 15 to 1000 ppm by weight. The upper limit value of the methylcyclopentanol concentration is more preferably 250 ppm by weight or less, and still more preferably 150 ppm by weight or less. When the methylcyclopentanol concentration in the purified cyclohexanol is the upper limit value or less, the coloration of adipic acid (hereinafter, also described as an "adipic acid product") obtained from the purified cyclohexanol is suppressed to result in high quality.

Therefore, in order to obtain the high-quality adipic acid product, the methylcyclopentanol concentration in the purified cyclohexanol is preferably lower. The purified cyclohexanol can be purified to have a methylcyclopentanol concentration therein at less than 10 ppm. However, even when the methylcyclopentanol concentration is less than 10 ppm, further improvement in the melting color number of the adipic acid product is not found, and the yield of the purified cyclohexanol is reduced. Therefore, the methylcyclopentanol concentration in the purified cyclohexanol is preferably 10 ppm or more from the viewpoint of the balance between the melting color number of the adipic acid product and the yield of cyclohexanol.

The purified cyclohexanol of the present embodiment has a cyclohexylcyclohexene isomer concentration of 15 to 500 ppm by weight. The upper limit value of the cyclohexylcyclohexene isomer concentration is more preferably 300 ppm by weight or less. The cyclohexylcyclohexene isomer is also a compound causing the coloration of the adipic acid product. Therefore, in order to obtain the high-quality adipic acid product, the cyclohexylcyclohexene isomer concentration is preferably lower. The cyclohexylcyclohexene isomer concentration in the purified cyclohexanol is preferably 15 ppm or more from the viewpoint of the balance between the melting color number of the adipic acid product and the yield of cyclohexanol.

The "cyclohexylcyclohexene isomer" in the present specification refers to all isomers of cyclohexylcyclohexene. When cyclohexanol is produced by the hydration reaction of cyclohexene, for example, a part of cyclohexene is considered to be dimerized to produce the cyclohexylcyclohexene isomer. Because the cyclohexylcyclohexene isomer has a higher boiling point than that of cyclohexanol, the cyclohexylcyclohexene isomer can be separated by distillation. However, in the hydration reaction of cyclohexene, the amount of the cyclohexylcyclohexene isomer produced is usually a low amount of a few thousand ppm by weight. Therefore, in the conventional purifying method, the cyclohexylcyclohexene isomer is not separated from cyclohexanol in many cases. However, according to the investigation by the present inventors, the cyclohexylcyclohexene isomer has a double bond, and has absorption in a visible region, which causes the coloration of the adipic acid product. Therefore, the cyclohexylcyclohexene isomer concentration in the purified cyclohexanol is preferably 15 to 500 ppm by weight from the viewpoint of producing adipic acid satisfying the melting color number.

Specific examples of the cyclohexylcyclohexene isomer include, but not particularly limited to, cyclohexyl-2-cyclohexene.

In the present embodiment, the methylcyclopentanol concentration and the cyclohexylcyclohexene isomer concentration in the purified cyclohexanol can be measured by gas chromatography on a capillary column. Specifically, for example, the concentrations can be measured as follows.

A withdrawing line for withdrawing a liquid and a sluice valve are installed in a line into which the liquid to be analyzed flows. When the sluice valve is opened, the liquid can be sampled from the withdrawing line. The methylcyclopentanol concentration and the cyclohexylcyclohexene isomer concentration in the liquid can be measured by sampling a liquid in an amount (at least 10 ml) that allows analysis by gas chromatography, and analyzing the sampled liquid under the following conditions by gas chromatography.

The gas chromatography conditions are not limited only to the following conditions. However, if the liquid is not analyzed under suitable conditions, the methylcyclopentanol concentration and the cyclohexylcyclohexene isomer concentration may be unable to be measured.

<Gas Chromatography Conditions>
1) Model: Shimadzu 2014AF$_{SC}$ (FID)
2) Column: Capillary Column (CBP20-S50-050)
3) Temperature: The temperature is held at 80° C. for 15 minutes, then increased at a rate of 5° C./minute, and held for 5 minutes after the temperature reaches 140° C. The temperature is held for 5 minutes, then reincreased at a rate of 5° C./minute, and held at 190° C. for 18 minutes.
    INJ.: 200° C.
    DET.: 220° C.
4) Carrier Gas: Helium
5) Split Ratio: 1/70
6) RANG: 10
7) Amount to Be Injected: 1 μl The purified cyclohexanol of the present embodiment in which the methylcyclopentanol concentration and the cyclohexylcyclohexene isomer concentration are in the above-mentioned specific ranges can be obtained by a method for producing cyclohexanol to be described later, for example.

<<Method for Producing Cyclohexanol>>

A method for producing cyclohexanol of the present embodiment comprises:

Step 1 of producing a solution (I) containing cyclohexanol, methylcyclopentanol, and water by a hydration reaction of cyclohexene;

Step 2 of separating the solution (I) into a water phase and an oil phase;

Step 3 of obtaining a partially purified cyclohexanol containing methylcyclopentanol from the oil phase; and Step 4 of separating and removing methylcyclopentanol in the partially purified cyclohexanol so as to obtain a purified cyclohexanol having a methylcyclopentanol concentration of 10 to 1000 ppm by weight and a cyclohexylcyclohexene isomer concentration of 15 to 500 ppm by weight.

[1] Hydration Reaction of Cyclohexene (Step 1)

The Step 1 is a step of producing a solution (I) containing cyclohexanol, methylcyclopentanol, and water by a hydration reaction of cyclohexene.

A catalyst for the hydration reaction of cyclohexene is not particularly limited. However, for example, a crystalline aluminosilicate can be utilized. Specific examples of the crystalline aluminosilicate include, but not particularly limited to, mordenite, faujasite, clinoptilolite, L-form zeolite, ZSM-type zeolite, chabazite, and erionite. AZ-1 (Japanese Patent Application No. 57-228283), TPZ-3 (Japanese Patent Laid-Open No. 58-110419), Nu-3 (Japanese Patent Laid-Open No. 57-3714), Nu-5 (Japanese Patent Laid-Open No. 57-129820), Nu-6 (Japanese Patent Laid-Open No. 57-123817), and Nu-10 (Japanese Patent Laid-Open No. 57-200218) or the like are also effective as the catalyst for the hydration reaction of cyclohexene.

The crystalline aluminosilicate preferably has a larger surface area from the viewpoint of catalytic activity. Therefore, the crystalline aluminosilicate preferably has a primary particle size of 0.5 μm or less, more preferably 0.1 μm or less, and still more preferably 0.05 μm or less. The lower limit of the primary particle size is not particularly limited. However, as long as the crystalline aluminosilicate has "crystallinity," the smallness of the primary particle size is limited.

"Crystal" in the present specification means one having atoms regularly and periodically arranged with the atoms having a certain symmetric property, wherein a diffraction phenomenon due to X-rays is observed (described in the item of "Crystal" on page 349 in Kagaku Daijiten, published in 1963, Vol. 3, Kyoritsu Shuppan Co., Ltd.). A finite size based on a crystal structure exists in order to have a fixed period and an observed X-ray diffraction phenomenon. It is preferable that the crystalline aluminosilicate used as the catalyst for the hydration reaction of cyclohexene has an observed X-ray diffraction phenomenon and a primary particle size of 0.5 μm or less.

The primary particle of the crystalline aluminosilicate exists in various states. However, in the present specification, the primary particle size of the crystalline aluminosilicate means a value obtained by measuring a diameter of a portion having the narrowest width of a particle to be measured observed by a scanning electron microscope and determining a value at which a proportion of particles having the measured numerical value or less based on the total amount of particles is at least 50% by quantity. When the primary particle size is 0.5 μm or less, a secondary particle of the crystalline aluminosilicate generated by the aggregation of the primary particles and having a larger diameter also exhibits an excellent catalytic ability in the hydration reaction based on the present inventors' findings.

Usually, in the hydration reaction of cyclic olefin, side reactions such as isomerization and polymerization occur. For example, in the hydration reaction of cyclohexene, by-products such as methylcyclopentenes, dicyclohexyl ether, and bicyclohexyl are produced. In order to suppress such side reactions and obtain a cyclic alcohol with high yield, it is also effective to use as a catalyst, for example, a crystalline aluminosilicate ZSM-5 disclosed in Japanese Patent Publication No. 4-41131. The crystalline aluminosilicate ZSM-5 is a zeolite developed by Mobil Oil Corporation (refer to U.S. Pat. No. 3,702,886), for which the molar ratio of silica and alumina (silica/alumina) constituting the crystal is 20 or more and which has three-dimensional pores having inlets of 10-membered oxygen-containing rings in the crystal structure.

The temperature of the hydration reaction of cyclohexene is advantageously low from the viewpoints of the equilibrium of the hydration reaction of cyclohexene and the suppression of the side reactions. However, if the reaction temperature is too low, the reaction rate is decreased, which is not economical. Therefore, the reaction temperature is preferably in the range of from 50° C. to 300° C. The applicable pressure of the hydration reaction of cyclohexene is from a decreased pressure to an increased pressure.

However, a pressure allowing both cyclohexene and water which are reaction raw materials to maintain a liquid phase is preferable. When the reaction temperature is 50° C. to 300° C. in the hydration reaction of cyclohexene, the reaction pressure is preferably 0 MPaG to 20 MPaG.

The molar ratio of cyclohexene and water which are the reaction raw materials can be in a wide range. However, excessive cyclohexene decreases the conversion of cyclohexene. Excessive water can increase the conversion of cyclohexene. However, it is disadvantageous from the viewpoints of separation and purification of cyclohexanol, and has the necessity of enlarging the volume of a reactor, which is not economical. Therefore, the molar ratio of water and cyclohexene (water/cyclohexene) is preferably 0.01 to 200.

The weight ratio of cyclohexene and the catalyst varies with conditions such as a reaction temperature, a reaction pressure, and a molar ratio of cyclohexene and water in a continuous reaction. However, generally, the weight of the catalyst is preferably in the range of from 0.005 to 200 based on the weight of cyclohexene fed to the reactor in 1 hour.

[2] Purification of Hydration Reaction Product (Steps 2 and 3)

The Step 2 is a step of separating the solution (I) produced in the Step 1 into a water phase and an oil phase.

Because the reaction raw material for the hydration reaction of cyclohexene mainly contains cyclohexene and water as described above, the product after the reaction also contains an oil phase and a water phase. Therefore, the solution (I) produced in the Step 1 is first separated into the oil phase and the water phase by, for example, liquid-liquid separation.

The oil phase is a liquid containing, for example, cyclohexanol, methylcyclopentanol, cyclohexene, impurities accompanied by cyclohexene, a low-boiling point substance and a high-boiling point substance by-produced in an ultralow amount during a hydration reaction, and a catalyst in an ultralow amount. Therefore, a method for industrially obtaining cyclohexanol as a product generally includes concentrating and purifying cyclohexanol by the operation such as distillation to obtain a product, recovering and recycling unreacted cyclohexene, and separating and removing impurities such as a high-boiling point substance and a catalyst.

FIG. 1 shows an example of an apparatus for producing cyclohexanol. The apparatus shown in FIG. 1 comprises a reactor 1, a separator 2 connected to the reactor 1, and a plurality of distillation columns 3, 4, and 5 serially connected to the downstream side of the separator 2.

A crystalline aluminosilicate which is a catalyst is stored in the reactor 1. Cyclohexene is fed from a raw material feed pipe 6. Water is fed from a raw material feed pipe 7. In the reactor 1, a temperature and a pressure suitable for a hydration reaction are set. The reaction of cyclohexene and water flowing into the reactor 1 progresses. In the example shown in FIG. 1, a reaction liquid remaining for a certain period of time in the reactor 1 to progress the hydration reaction continuously flows into the separator 2 from the reactor 1. Cyclohexene and water in an amount corresponding to the outflow are fed to the reactor 1.

Hereinafter, the Step 2 will be specifically described by taking the apparatus for producing cyclohexanol shown in FIG. 1 as an example.

The solution (I) produced in the hydration reaction of cyclohexene in the Step 1 contains the oil phase and the water phase. While the solution (I) is left at rest in the separator 2, the solution (I) is separated into the two phases. Because a pipe 10 is provided at a position higher than the oil water interface level of the separator 2, only the oil phase which is an upper layer flows out to the downstream distillation column from the separator 2. The oil phase contains, for example, cyclohexanol, cyclohexene, impurities accompanied by cyclohexene, a low-boiling point substance and a high-boiling point substance by-produced in an ultralow amount during a hydration reaction, a catalyst in an ultralow amount, and methylcyclopentanol. Generally, a cyclohexanol concentration in the oil phase is, for example, 8 to 15% by weight. A return pipe 9 provided on the bottom part of the separator 2 is connected to the bottom part of the reactor 1. A slurried catalyst is recycled to the reactor 1 via the return pipe 9 with a part of the water phase from the bottom part of the separator 2.

The Step 3 is a step of obtaining a partially purified cyclohexanol containing methylcyclopentanol from the oil phase. The partially purified cyclohexanol can be obtained by separating and removing the impurities from the oil phase using the distillation column, for example.

Hereinafter, the Step 3 will be specifically described by taking the apparatus for producing cyclohexanol shown in FIG. 1 as an example.

The oil phase flowing out from the separator 2 is fed to the distillation column 3 via the pipe 10. The impurities are crudely separated and removed from the oil phase in the distillation column 3. The distillation columns 3 and 4 are, for example, multistage, and have the number of theoretical plates of 10 or more, and more preferably 20 or more (a condenser and a reboiler each are also regarded as one plate; hereafter the same applies).

A reflux ratio is preferably 1 to 20 from the viewpoint of recovering unreacted cyclohexene.

The oil phase in which cyclohexanol is concentrated to, for example, 40 to 60% by weight by the distillation column 3 is withdrawn from a pipe 12 as a bottom liquid. The bottom liquid is fed to a middle part of the distillation column 4. A part of the top liquid is recycled to the reactor 1 via a pipe 11.

In the distillation column 4, the concentration of cyclohexanol in the oil phase received from the pipe 12 is further concentrated, and thereby the partially purified cyclohexanol can be obtained. The concentration of cyclohexanol in the partially purified cyclohexanol is preferably 95 to 99.8% by weight, more preferably 97 to 99.8% by weight, and still more preferably 98 to 99.8% by weight. The partially purified cyclohexanol in which cyclohexanol is concentrated to, for example, 95 to 99.8% by weight is fed to the distillation column 5 via a pipe 15 provided at a position lower than the connection position of the pipe 12.

In order to increase the concentration of cyclohexanol in the partially purified cyclohexanol to a suitable range, the temperature of the pipe 15 is preferably managed to 143 to 161° C. (in the case of an atmosphere pressure). From the viewpoints of increasing the concentration of cyclohexanol to the suitable range and of recovering unreacted cyclohexene from the top, for example, in the distillation column 4 having the number of theoretical plates of 15, the connection position of the pipe 15 is preferably provided at a position lower than the connection position of the pipe 12 by 5 plates or more, and more preferably provided at a position lower by 10 plates or more. The connection position of the pipe 15 is preferably provided at a position higher than the connection position (inflow place) of a pipe 14 by 0.2 plates or more, and more preferably provided at a position higher by 1 plate or more.

Dicyclohexyl ether and the cyclohexylcyclohexene isomer which are by-produced in the hydration reaction of cyclohexene can be separated from cyclohexanol by withdrawing the partially purified cyclohexanol not from the bottom but from the middle part (pipe 15) in the distillation column 4. The concentration of the cyclohexylcyclohexene isomer in the partially purified cyclohexanol withdrawn from the pipe 15 is preferably 15 to 500 ppm by weight, more preferably 15 to 300 ppm by weight, and still more preferably 15 to 200 ppm by weight. The cyclohexylcyclohexene isomer concentration in the partially purified cyclohexanol withdrawn from the pipe 15 can also be technically set to be less than 15 ppm by weight. However, this lengthens the time for heating cyclohexanol to further produce the high-boiling point component, resulting in the reduction in the productivity of cyclohexanol. Therefore, from the viewpoint of the productivity of cyclohexanol, the cyclohexylcyclohexene isomer concentration in the partially purified cyclohexanol withdrawn from the pipe 15 is preferably 15 ppm by weight or more. The partially purified cyclohexanol is preferably withdrawn from the middle part (pipe 15) of the distillation column 4 in the Step 3 because of the same reason as the above description. The bottom liquid of the distillation column 4 usually contains a catalyst and cyclohexanol. However, the bottom liquid is withdrawn out of the system via the pipe 14 for the purpose of withdrawing cyclohexyl ether and the concentrated cyclohexylcyclohexene isomer.

[3] Separation of Methylcyclopentanol (Step 4)

The Step 4 is a step of separating and removing methylcyclopentanol in the partially purified cyclohexanol so as to obtain a purified cyclohexanol having a methylcyclopentanol concentration of 10 to 1000 ppm by weight and a cyclohexylcyclohexene isomer concentration of 15 to 500 ppm by weight.

In the Step 4, a distillation column is preferably used as an apparatus separating and removing methylcyclopentanol.

Hereinafter, the Step 4 will be specifically described by taking the apparatus for producing cyclohexanol shown in FIG. 1 as an example.

In the distillation column 5, methylcyclopentanol in the partially purified cyclohexanol is separated and removed.

From the viewpoint of easily separating methylcyclopentanol, the distillation column 5 preferably has the number of theoretical plates of 40 or more, and more preferably 50 or more. From the viewpoint of concentrating methylcyclopentanol at the top, for example, the pipe 15 is preferably connected to the middle part (for example, 25th to 35th plates) of the distillation column 5 having the number of theoretical plates of 50. The partially purified cyclohexanol introduced into the distillation column 5 from the pipe 15 preferably contains 95 to 99.8% by weight of cyclohexanol and 1500 to 20000 ppm by weight of methylcyclopentanol. The partially purified cyclohexanol more preferably contains 97 to 99.8% by weight of cyclohexanol and 1500 to 20000 ppm by weight of methylcyclopentanol, and still more preferably 98 to 99.8% by weight of cyclohexanol and 1500 to 10000 ppm by weight of methylcyclopentanol. The contents of cyclohexanol and methylcyclopentanol in the partially purified cyclohexanol introduced into the distillation column 5 are set to be within the above ranges, and thereby the amount of the used steam of the distillation column 5 tends to be decreased, which is preferable.

In the present embodiment, the contents of cyclohexanol and methylcyclopentanol in the partially purified cyclohexanol can be measured by gas chromatography using a capillary column. The details of the measuring method are the same as those of the method for measuring the methylcyclopentanol concentration and the cyclohexylcyclohexene isomer concentration.

The reflux ratio is preferably 100 to 5000.

In the distillation column 5, a top distillate component having an increased concentration, for example, 30 to 80% by weight of methylcyclopentanol is withdrawn from a pipe 16. Thereby, the purified cyclohexanol in which the methylcyclopentanol concentration is 10 to 1000 ppm by weight is obtained from a pipe 17 of the bottom.

In the distillation column 5, methylcyclopentanol is concentrated and withdrawn from the top. Since an insufficient concentration causes a loss of the purified cyclohexanol as a product, the concentration management of methylcyclopentanol is preferably performed from the index of economic efficiency. In the case of general distillation, the concentration management of methylcyclopentanol is performed only by the reflux ratio. However, a small amount of impurities are withdrawn in the distillation column 5, which may decrease the amount to be withdrawn of the pipe 16 and cause the instability of the reflux ratio. Then, for example, the temperature of the vicinity of the top (for example, the second to fifth plates from the top) of the distillation column 5 having the number of theoretical plates of 50 is preferably controlled to 144 to 154° C. (700 mmHg), more preferably 144 to 152° C. (700 mmHg), and still more preferably 144 to 150° C. (700 mmHg), and thereby the concentration management of methylcyclopentanol is preferably performed.

[4] Cyclohexanol

In the case of a method (hereinafter, also described as a "cyclohexene method") of obtaining cyclohexanol in the hydration reaction of cyclohexene, the partially purified cyclohexanol usually contains a low amount of methylcyclopentanol as described above. Depending on conditions, the partially purified cyclohexanol may contain about 1500 ppm by weight of methylcyclopentanol. A product using the partially purified cyclohexanol causes problems in some applications. The reason why the partially purified cyclohexanol contains methylcyclopentanol in the case of the cyclohexene method is as follows. A part of cyclohexene is isomerized in the hydration reaction to become methylcyclopentene, and the methylcyclopentene is hydrated to produce methylcyclopentanol. Because methylcyclopentanol has a boiling point close to that of cyclohexanol, methylcyclopentanol cannot be removed by a normal distillation method which is industrially performed.

On the other hand, the method for producing cyclohexanol of the present embodiment separates and removes methylcyclopentanol in the partially purified cyclohexanol in the above-mentioned specific Step 4, and thereby the purified cyclohexanol in which the methylcyclopentanol concentration is 10 to 1000 ppm by weight can be obtained. Examples of a method for controlling the methylcyclopentanol concentration of 10 to 1000 ppm by weight include a method using a dedicated distillation column for separating methylcyclopentanol as for the above-mentioned distillation column 5.

For example, the methylcyclopentanol concentration in the purified cyclohexanol can also be set to be less than 10 ppm by weight by distillation operation in the distillation column 5. However, to that end, it is necessary to increase an amount to be withdrawn from the top of the distillation column 5. Then, the cyclohexylcyclohexene isomer and methyl cyclohexanol which cannot be separated in the distillation column 5 are concentrated. Therefore, in the purified cyclohexanol obtained from the bottom, the contents of the cyclohexylcyclohexene isomer and methyl cyclohexanol are increased. When the purified cyclohexanol is used as an adipic acid raw material, the cyclohexylcyclohexene isomer and methyl cyclohexanol cause the deterioration of the quality of adipic acid. Therefore, from the viewpoint of obtaining high-quality adipic acid, the methylcyclopentanol concentration in the purified cyclohexanol is set to be 10 ppm by weight or more.

The contents of pentanol and methyl cyclohexanol in cyclohexanol obtained by the cyclohexene method are less than those by a cyclohexane method. Pentanol and methyl cyclohexanol may produce a compound hardly separated, in the production process of adipic acid to influence the quality of adipic acid. However, for example, pentanol is separated and removed as for methylcyclopentanol by the distillation operation in the distillation column 5, and a pentanol concentration in the purified cyclohexanol is set to be lower than that in the partially purified cyclohexanol. Therefore, the purified cyclohexanol which is produced by the cyclohexane method and in which the methylcyclopentanol concentration is suitably controlled to the above-mentioned specific range is suitable as a raw material for obtaining the high-quality adipic acid.

<<Method for Producing Adipic Acid>>

A method for producing adipic acid of the present embodiment comprises a step of oxidizing a purified cyclohexanol having a methylcyclopentanol concentration of 10 to 1000 ppm by weight and a cyclohexylcyclohexene isomer concentration of 15 to 500 ppm by weight by nitric acid. The high-quality adipic acid having an excellent melting color number can be obtained by using as a raw materials the purified cyclohexanol in which the methylcyclopentanol concentration and the cyclohexylcyclohexene isomer concentration are controlled to the specific ranges.

The method for producing adipic acid of the present embodiment preferably comprises a crystallizing-purifying step after the step of oxidizing the purified cyclohexanol by nitric acid.

The nitric acid oxidation reaction of the purified cyclohexanol is progressed by feeding the purified cyclohexanol into an excessive amount of a nitric acid aqueous solution. Herein, the nitric acid aqueous solution is an aqueous solution having a nitric acid concentration of 10 to 70%. The nitric acid aqueous solution is preferably an aqueous solution having a nitric acid concentration of 50 to 65%. The nitric acid aqueous solution preferably contains copper and vanadium as catalysts.

The reaction temperature of the nitric acid oxidation reaction of the purified cyclohexanol is preferably 60 to 100° C.

The crystallizing-purifying step is, for example, a step of cooling a nitric acid aqueous solution containing a nitric acid oxidation reaction product to a room temperature to crystallize adipic acid, and thereafter obtaining a crude adipic acid crystal by filtration. A purified adipic acid is obtained by placing the obtained crude adipic acid crystal in pure water, dissolving the crude adipic acid crystal in the pure water, and performing crystallization, solid liquid separation, and drying. Upon the crystallization, the solution may be stirred or heated to dissolve the crude adipic acid crystal. The solution may be aged for a suitable time to grow the crystal. A suitable condition may be selected at the melting point of adipic acid or lower as the drying condition.

It became clear that the melting color number of adipic acid as the obtained product was remarkably impaired when adipic acid was produced by using the partially purified cyclohexanol containing more than 1000 ppm by weight of methylcyclopentanol according to the investigations conducted by the present inventors. As one of the causes, the present inventors presume that dicarboxylic acids produced in the nitric acid oxidation reaction step from methylcyclopentanol remaining in the partially purified cyclohexanol suppress the crystal growth of adipic acid in the purifying step by the crystallization of the crude adipic acid, to inhibit the purification of adipic acid, and as a result, a adipic acid product having a satisfied quality cannot be obtained.

The melting color number of adipic acid is measured as follows based on Japanese Industrial Standards JIS K4172. In the production of adipic acid, the melting color number is utilized as the index of coloration.

[Measurement of Melting Color Number (Quality Measurement)]

25 g of a purified adipic acid is placed in a test tube, and melted in a melting apparatus adjusted to a temperature of 250±2° C. The melted purified adipic acid is compared with a Hazen color number (APHA) standard solution to measure a color number.

The purified cyclohexanol in which the methylcyclopentanol concentration is controlled to 10 to 1000 ppm by weight and the cyclohexylcyclohexene isomer concentration is controlled to 15 to 500 ppm by weight is used as a raw material, and thereby the obtained purified adipic acid has a good melting color number.

EXAMPLES

Hereinafter, the present invention will be further described in detail according to Examples. However, the present invention is not limited thereto so long as it is within the purport thereof. The amount of each of components such as methylcyclopentanol in Examples was determined by gas chromatography using a capillary column.

Example 1

[Hydration Reaction of Cyclohexene]

The hydration reaction of cyclohexene was carried out in the reactor 1 in FIG. 1.

A ZSM-5 particulate which was a crystalline aluminosilicate described in Japanese Patent Laid-Open No. 3-193622 as a catalyst was introduced into an autoclave equipped with stirrers, which was the reactor 1. The crystalline aluminosilicate was mixed with water with a weight ratio of water to crystalline aluminosilicate of 2:1 to obtain a slurried catalyst. The crystalline aluminosilicate had a primary particle size of 0.1 µm.

A gas phase portion was pressurized with nitrogen gas so that a reaction pressure was 6 kg/cm$^2$G with setting a reaction temperature at 125° C. and a number of stirrer revolutions at 530 rpm.

Cyclohexene was fed in an amount of 1 part by weight per hour based on 1 part by weight of the catalyst through the raw material feed pipe 6 of FIG. 1 to the reactor 1, and water was fed in an amount corresponding to the amount of water consumed in the reaction through the raw material feed pipe 7 to carry out the hydration reaction of cyclohexene, thereby producing a solution (I-1) containing cyclohexanol, methylcyclopentanol, and water.

[Separation Between Water Phase and Oil Phase]

The produced solution (I-1) was fed to the separator 2 through a pipe 8. The solution (I-1) was left at rest in the separator 2 to separate the solution (I-1) into a water phase and an oil phase.

The amount of the slurried catalyst returned to the reactor 1 via the return pipe 9 was adjusted so that the oil water interface level of the separator 2 was located lower than the pipe 10. Thereby, only the oil phase which was an upper layer was fed to the distillation column 3 via the pipe 10 from the separator 2.

The oil phase fed to the distillation column 3 via the pipe 10 was a mixture containing cyclohexanol and methylcyclopentanol. The mixture contained 2000 ppm by weight of methylcyclopentanol based on cyclohexanol. The yield of cyclohexanol was 11.0%.

[Purification of Cyclohexanol]

100 parts by weight of the separated oil phase was fed to the distillation column 3 via the pipe 10 to purify cyclohexanol. 88.198 parts by weight of a distillate was withdrawn from the top of the distillation column 3. The distillate was joined to the raw material feed pipe 6 via the pipe 11, and then recycled to the reactor 1. The composition of the distillate had 99.21% by weight of cyclohexene, 0.23% by weight of toluene, 0.30% by weight of norcamphane, and 0.26% by weight of methylcyclohexane.

The bottom liquid of the distillation column 3 was fed to the distillation column 4 via the pipe 12 to further purify cyclohexanol.

A catalyst and 0.500 parts by weight of cyclohexanol were withdrawn out of the system via the pipe 14 from the bottom of the distillation column 4. The distillate from the top of the distillation column 4 was recycled to the distillation column 3 via a return pipe 13. The composition of the distillate had 91.50% by weight of cyclohexene, 1.80% by weight of toluene, 2.50% by weight of norcamphane, 2.10% by weight of methylcyclohexane, and 2.10% by weight of cyclohexanol.

11.298 parts by weight of a partially purified cyclohexanol containing 2 ppm by weight of cyclohexene and 5 ppm by weight of toluene was obtained as steam from the pipe 15 provided below the connection part of the pipe 12 and the distillation column 4 above the connection part of the pipe 14 and the distillation column 4. The partially purified cyclohexanol contained 99.8% by weight of cyclohexanol, 1500 ppm by weight of methylcyclopentanol, 300 ppm by weight of a cyclohexylcyclohexene isomer, 50 ppm by weight of pentanol, and 50 ppm by weight of methyl cyclohexanol.

[Separation and Removal of Methylcyclopentanol]

The obtained partially purified cyclohexanol was fed to the distillation column 5 via the pipe 15 of a partially purified product. In the distillation column 5, methylcyclopentanol in the partially purified cyclohexanol was separated and removed. The temperature of the vicinity of the top (the second to fifth plates from the top) of the distillation column 5 having the number of theoretical plates of 50 was controlled to 149° C. (700 mmHg). 0.0027 parts by weight of the distillate from the top of the distillation column 5 was withdrawn out of the system via the pipe 16. The distillate contained 52% by weight of methylcyclopentanol. A purified cyclohexanol was obtained from the purified product withdrawing pipe 17 of the bottom of the distillation column 5. The purified cyclohexanol had a methylcyclopentanol concentration of 250 ppm by weight, a cyclohexylcyclohexene isomer concentration of 308 ppm by weight, a pentanol concentration of 1 ppm by weight or less, and a methyl cyclohexanol concentration of 51 ppm by weight.

[Synthesis of Adipic Acid]

The purified cyclohexanol was fed into an excessive amount of a nitric acid aqueous solution to carry out the nitric acid oxidation reaction of cyclohexanol. Herein, the nitric acid aqueous solution was an aqueous solution having a nitric acid concentration of 60%. The nitric acid aqueous solution was an aqueous solution containing a low amount of copper and vanadium.

The nitric acid oxidation reaction was carried out for 1 hour at a reaction pressure setting at an atmosphere pressure and a reaction temperature at 80° C.

Then, the nitric acid aqueous solution containing a reaction product was cooled to a room temperature to crystallize adipic acid. The aqueous solution was subjected to solid liquid separation by filtration to obtain a crude adipic acid crystal. Next, the crude adipic acid crystal was placed in pure water, heated, and dissolved. The solution was crystallized, subjected to solid liquid separation in the same manner as above, and dried to obtain a purified adipic acid.

[Quality Measurement]

25 g of the above-mentioned purified adipic acid was placed in a test tube, and melted in a melting apparatus adjusted to a temperature of 250±2° C. The melted purified adipic acid was compared with a Hazen color number (APHA) standard solution, to measure a color number (based on Japanese Industrial Standards JIS K4172). The melting color number of the above-mentioned purified adipic acid was 10 APHA or less.

Example 2

A partially purified cyclohexanol (cyclohexanol concentration: 99.8% by weight, methylcyclopentanol concentration: 1500 ppm by weight, cyclohexylcyclohexene isomer concentration: 300 ppm by weight, pentanol concentration: 50 ppm by weight, methyl cyclohexanol concentration: 50 ppm by weight) obtained by the same operation as that of Example 1 was fed to the distillation column 5 from the pipe 15. In the distillation column 5, methylcyclopentanol in the partially purified cyclohexanol was separated and removed. The temperature of the vicinity of the top (the second to fifth plates from the top) of the distillation column 5 having the number of theoretical plates of 50 was controlled to 146° C. (700 mmHg). 0.0024 parts by weight of a distillate from the top of the distillation column 5 was withdrawn out of the system via the pipe 16. The distillate contained 70% by weight of methylcyclopentanol. A purified cyclohexanol was obtained from the purified product withdrawing pipe 17 of the bottom of the distillation column 5. The purified cyclohexanol had a methylcyclopentanol concentration of 15 ppm by weight, a cyclohexylcyclohexene isomer concentration of 301 ppm by weight, a pentanol concentration of 1 ppm by weight or less, and a methyl cyclohexanol concentration of 50 ppm by weight.

Adipic acid was synthesized by the same method as that of Example 1 except that the obtained purified cyclohexanol was used, and the quality measurement of the obtained purified adipic acid was carried out.

The melting color number of the obtained purified adipic acid was 10 APHA or less.

Example 3

A partially purified cyclohexanol (cyclohexanol concentration: 99.8% by weight, methylcyclopentanol concentration: 1500 ppm by weight, cyclohexylcyclohexene isomer concentration: 300 ppm by weight, pentanol concentration: 50 ppm by weight, methyl cyclohexanol concentration: 50 ppm by weight) obtained by the same operation as that of Example 1 was fed to the distillation column 5 from the pipe 15. In the distillation column 5, methylcyclopentanol in the partially purified cyclohexanol was separated and removed. The temperature of the vicinity of the top (the second to fifth plates from the top) of the distillation column 5 having the number of theoretical plates of 50 was controlled to 155° C. (700 mmHg). 0.0074 parts by weight of a distillate from the top of the distillation column 5 was withdrawn out of the system via the pipe 16. The distillate contained 75% by weight of methylcyclopentanol. A purified cyclohexanol was obtained from the purified product withdrawing pipe 17 of the bottom of the distillation column 5. The purified cyclohexanol had a methylcyclopentanol concentration of 15 ppm by weight, a cyclohexylcyclohexene isomer concentration of 302 ppm by weight, a pentanol concentration of 1 ppm by weight or less, and a methyl cyclohexanol concentration of 50 ppm by weight.

Adipic acid was synthesized by the same method as that of Example 1 except that the obtained purified cyclohexanol was used, and the quality measurement of the obtained purified adipic acid was carried out.

The melting color number of the obtained purified adipic acid was 10 APHA or less.

Example 4

A partially purified cyclohexanol (cyclohexanol concentration: 99.8% by weight, methylcyclopentanol concentration: 1500 ppm by weight, cyclohexylcyclohexene isomer concentration: 300 ppm by weight, pentanol concentration: 50 ppm by weight, methyl cyclohexanol concentration: 50 ppm by weight) obtained by the same operation as that of Example 1 was fed to the distillation column 5 from the pipe 15. In the distillation column 5, methylcyclopentanol in the partially purified cyclohexanol was separated and removed. The temperature of the vicinity of the top (the second to fifth plates from the top) of the distillation column 5 having the number of theoretical plates of 50 was controlled to 156° C. (700 mmHg). 0.13 parts by weight of a distillate from the top of the distillation column 5 was withdrawn out of the system via the pipe 16. The distillate contained 13% by weight of methylcyclopentanol. A purified cyclohexanol was obtained from the purified product withdrawing pipe 17 of the bottom of the distillation column 5. The purified cyclohexanol had a methylcyclopentanol concentration of 15 ppm by weight, a cyclohexylcyclohexene isomer concentration of 344 ppm by weight, a pentanol concentration of 1 ppm by weight or less, and a methyl cyclohexanol concentration of 57 ppm by weight.

Adipic acid was synthesized by the same method as that of Example 1 except that the obtained purified cyclohexanol was used, and the quality measurement of the obtained purified adipic acid was carried out.

The melting color number of the obtained purified adipic acid was 10 APHA or less.

Example 5

The same operation as that in Example 1 was carried out until the purifying operation of cyclohexanol in the distillation column 3 to obtain a bottom liquid of the distillation column 3.

Cyclohexanol was further purified in the same manner as in Example 1 except that the bottom liquid of the distillation column 3 was fed to the distillation column 4 via the pipe 12 to change a separation state in the distillation column 4.

A catalyst and 0.500 parts by weight of cyclohexanol were withdrawn out of the system via the pipe 14 from the bottom of the distillation column 4. A distillate from the top of the distillation column 4 was recycled to the distillation column 3 via the return pipe 13. The composition of the distillate had 86.50% by weight of cyclohexane, 1.80% by weight of toluene, 2.50% by weight of norcamphane, 2.10% by weight of methylcyclohexane, and 7.10% by weight of cyclohexanol.

11.2 parts by weight of a partially purified cyclohexanol containing 2 ppm by weight of cyclohexene and 5 ppm by weight of toluene was obtained as steam from the pipe 15 provided below the connection part of the pipe 12 and the distillation column 4 above the connection part of the pipe 14 and the distillation column. The partially purified cyclohexanol had a cyclohexanol concentration of 98% by weight, a methylcyclopentanol concentration of 3500 ppm by weight, a cyclohexylcyclohexene isomer concentration of 300 ppm by weight, a pentanol concentration of 50 ppm by weight, and a methyl cyclohexanol concentration of 50 ppm by weight.

The partially purified cyclohexanol obtained above was fed to the distillation column 5 from the pipe 15. In the distillation column 5, methylcyclopentanol in the partially purified cyclohexanol was separated and removed. The temperature of the vicinity of the top (the second to fifth plates from the top) of the distillation column 5 having the number of theoretical plates of 50 was controlled to 146° C. (700 mmHg). 0.0046 parts by weight of the distillate from the top of the distillation column 5 was withdrawn out of the system via the pipe 16. The distillate contained 75% by weight of methylcyclopentanol. A purified cyclohexanol was obtained from the purified product withdrawing pipe 17 of the bottom of the distillation column 5. The purified cyclohexanol had a methylcyclopentanol concentration of 15 ppm by weight, a pentanol concentration of 1 ppm by weight or less, a cyclohexylcyclohexene isomer concentration of 301 ppm by weight, and a methyl cyclohexanol concentration of 50 ppm by weight.

Adipic acid was synthesized by the same method as that of Example 1 except that the obtained purified cyclohexanol was used, and the quality measurement of the obtained purified adipic acid was carried out.

The melting color number of the obtained purified adipic acid was 10 APHA or less.

Example 6

A partially purified cyclohexanol (cyclohexanol concentration: 98% by weight, methylcyclopentanol concentration: 3500 ppm by weight, cyclohexylcyclohexene isomer concentration: 300 ppm by weight, pentanol concentration: 50 ppm by weight, methyl cyclohexanol concentration: 50 ppm by weight) obtained by the same operation as that of Example 5 was fed to the distillation column 5 from the pipe 15. In the distillation column 5, methylcyclopentanol in the partially purified cyclohexanol was separated and removed. The temperature of the vicinity of the top (the second to fifth plates from the top) of the distillation column 5 having the number of theoretical plates of 50 was controlled to 155° C. (700 mmHg). 0.0136 parts by weight of a distillate from the top of the distillation column 5 was withdrawn out of the system via the pipe 16. The distillate contained 75% by weight of methylcyclopentanol. A purified cyclohexanol was obtained from the purified product withdrawing pipe 17 of the bottom of the distillation column 5. The purified cyclohexanol had a methylcyclopentanol concentration of 15 ppm by weight, a pentanol concentration of 1 ppm by weight or less, a cyclohexylcyclohexene isomer concentration of 304 ppm by weight, and a methyl cyclohexanol concentration of 51 ppm by weight.

Adipic acid was synthesized by the same method as that of Example 1 except that the obtained purified cyclohexanol was used, and the quality measurement of the obtained purified adipic acid was carried out.

The melting color number of the obtained purified adipic acid was 10 APHA or less.

Example 7

A partially purified cyclohexanol (cyclohexanol concentration: 98% by weight, methylcyclopentanol concentration: 3500 ppm by weight, cyclohexylcyclohexene isomer concentration: 300 ppm by weight, pentanol concentration: 50 ppm by weight, methyl cyclohexanol concentration: 50 ppm by weight) obtained by the same operation as that of Example 5 was fed to the distillation column 5 from the pipe 15. In the distillation column 5, methylcyclopentanol in the partially purified cyclohexanol was separated and removed. The temperature of the vicinity of the top (the second to fifth plates from the top) of the distillation column 5 having the number of theoretical plates of 50 was controlled to 158° C. (700 mmHg). 0.10 parts by weight of a distillate from the top of the distillation column 5 was withdrawn out of the system via the pipe 16. The distillate contained 75% by weight of methylcyclopentanol. A purified cyclohexanol was obtained from the purified product withdrawing pipe 17 of the bottom of the distillation column 5. The purified cyclohexanol had a methylcyclopentanol concentration of 15 ppm by weight, a pentanol concentration of 1 ppm by weight or less, a cyclohexylcyclohexene isomer concentration of 333 ppm by weight, and a methyl cyclohexanol concentration of 55 ppm by weight.

Adipic acid was synthesized by the same method as that of Example 1 except that the obtained purified cyclohexanol was used, and the quality measurement of the obtained purified adipic acid was carried out.

The melting color number of the obtained purified adipic acid was 10 APHA or less.

Example 8

Continuous operation was carried out for 1000 hours by the same operation as that of Example 1. A purified cyclohexanol was obtained from the purified product withdrawing pipe 17 of the bottom of the distillation column 5 after 1000 hours. The partially purified cyclohexanol had a methylcyclopentanol concentration of 15 ppm by weight, a cyclohexylcyclohexene isomer concentration of 300 ppm by weight, a pentanol concentration of 1 ppm by weight or less, and a methyl cyclohexanol concentration of 50 ppm by weight.

Adipic acid was synthesized by the same method as that of Example 1 except that the obtained partially purified cyclohexanol was used, and the quality measurement of the obtained purified adipic acid was carried out.

The melting color number of the obtained purified adipic acid was 10 APHA or less.

Comparative Example 1

Adipic acid was synthesized by the same method as that of Example 1 except that the partially purified cyclohexanol (cyclohexanol concentration: 99.8% by weight, methylcyclopentanol concentration: 1500 ppm by weight, cyclohexylcyclohexene isomer concentration: 300 ppm by weight, pentanol concentration: 100 ppm by weight, methyl cyclohexanol concentration: 50 ppm by weight) obtained from the pipe 15 in Example 1 was used as a synthesis raw material of adipic acid, and the quality measurement of the obtained purified adipic acid was carried out.

The melting color number of the obtained purified adipic acid was 100 APHA.

Comparative Example 2

A cyclohexanol-containing mixture (cyclohexanol concentration: 99.8% by weight, methylcyclopentanol concentration: 50 ppm by weight, cyclohexylcyclohexene isomer concentration: 1500 ppm by weight) was obtained from the pipe 14 in Example 1. Adipic acid was synthesized by the same method as that of Example 1 except that the cyclohexanol-containing mixture was used as a synthesis raw material of adipic acid, and the quality measurement of the obtained purified adipic acid was carried out.

The melting color number of the obtained purified adipic acid was 30 APHA.

Comparative Example 3

A partially purified cyclohexanol (cyclohexanol concentration: 99.8% by weight, methylcyclopentanol concentration: 1500 ppm by weight, cyclohexylcyclohexene isomer concentration: 300 ppm by weight, pentanol concentration: 50 ppm by weight, methyl cyclohexanol concentration: 50 ppm by weight) obtained by the same operation as that of Example 1 was fed to the distillation column 5 from the pipe 15. In the distillation column 5, methylcyclopentanol in the partially purified cyclohexanol was separated and removed. The temperature of the vicinity of the top (the second to fifth plates from the top) of the distillation column 5 having the number of theoretical plates of 50 was controlled to 158° C. (700 mmHg). 0.50 parts by weight of a distillate from the top of the distillation column 5 was withdrawn out of the system via the pipe 16. The distillate contained 0.7% by weight of methylcyclopentanol. A purified cyclohexanol was obtained from the purified product withdrawing pipe 17 of the bottom of the distillation column 5. The purified cyclohexanol had a methylcyclopentanol concentration of 1 ppm by weight or less, a cyclohexylcyclohexene isomer concentration of 600 ppm by weight, a pentanol concentration of 1 ppm by weight or less, and a methyl cyclohexanol concentration of 100 ppm by weight.

Adipic acid was synthesized by the same method as that of Example 1 except that the obtained purified cyclohexanol was used, and the quality measurement of the obtained purified adipic acid was carried out.

The melting color number of the obtained purified adipic acid was 30 APHA.

Comparative Example 4

A partially purified cyclohexanol (cyclohexanol concentration: 98% by weight, methylcyclopentanol concentration: 3500 ppm by weight, cyclohexylcyclohexene isomer concentration: 300 ppm by weight, pentanol concentration: 50 ppm by weight, methyl cyclohexanol concentration: 50 ppm by weight) obtained by the same operation as that of Example 5 was fed to the distillation column 5 from the pipe 15. In the distillation column 5, methylcyclopentanol in the partially purified cyclohexanol was separated and removed. The temperature of the vicinity of the top (the second to fifth plates from the top) of the distillation column 5 having the number of theoretical plates of 50 was controlled to 158° C. (700 mmHg). 0.50 parts by weight of a distillate from the top of the distillation column 5 was withdrawn out of the system via the pipe 16. The distillate contained 0.7% by weight of methylcyclopentanol. A purified cyclohexanol was obtained from the purified product withdrawing pipe 17 of the bottom of the distillation column 5. The purified cyclohexanol had a methylcyclopentanol concentration of 1 ppm by weight or less, a cyclohexylcyclohexene isomer concentration of 600 ppm by weight, a pentanol concentration of 1 ppm by weight or less, and a methyl cyclohexanol concentration of 100 ppm by weight.

Adipic acid was synthesized by the same method as that of Example 1 except that the obtained purified cyclohexanol was used, and the quality measurement of the obtained purified adipic acid was carried out.

The melting color number of the obtained purified adipic acid was 30 APHA.

Comparative Example 5

A cyclohexanol-containing mixture (cyclohexanol concentration: 99.8% by weight, methylcyclopentanol concentration: 50 ppm by weight, cyclohexylcyclohexene isomer concentration: 1500 ppm by weight) was obtained from the pipe 14 by the same operation as that of Example 1 except that a production apparatus shown in FIG. 2 was used as a production apparatus. As shown in FIG. 2, the cyclohexanol-containing mixture was fed to the distillation column 5 from the pipe 14, and continuous operation was carried out. Because the distillation column was in an unstable operation state after a lapse of about 50 hours, the continuous operation was stopped after 100 hours. A purified cyclohexanol was obtained from the top of the distillation column 5 after 100 hours. The purified cyclohexanol had a methylcyclopentanol concentration of 50 ppm by weight, a pentanol concentration of 1 ppm by weight or less, a methyl cyclohexanol concentration of 50 ppm by weight, and a cyclohexylcyclohexene isomer concentration of 1000 ppm.

Adipic acid was synthesized by the same method as that of Example 1 except that the obtained purified cyclohexanol was used, and the quality measurement of the obtained purified adipic acid was carried out.

The melting color number of the obtained purified adipic acid was 20 APHA.

After the distillation column 5 after the above-mentioned continuous operation was opened, deposited materials were observed on the lower part of the distillation column. The deposited materials are considered to be produced by the reaction of a cyclohexylcyclohexene isomer or the like. The materials caused the clogging of the distillation column, which inhibited stable operation.

TABLE 1

| Quality evaluation of purified adipic acid | Melting color number APHA |
| --- | --- |
| Example 1 | 10 or less |
| Example 2 | 10 or less |
| Example 3 | 10 or less |
| Example 4 | 10 or less |
| Example 5 | 10 or less |
| Example 6 | 10 or less |
| Example 7 | 10 or less |
| Example 8 | 10 or less |
| Comparative Example 1 | 100 |

TABLE 1-continued

| Quality evaluation of purified adipic acid | Melting color number APHA |
| --- | --- |
| Comparative Example 2 | 30 |
| Comparative Example 3 | 30 |
| Comparative Example 4 | 30 |
| Comparative Example 5 | 20 |

The present application is based on a Japanese patent application filed on Jul. 12, 2011 (Japanese Patent Application No. 2011-154023), whose contents are hereby incorporated by reference herein.

INDUSTRIAL APPLICABILITY

The purified cyclohexanol of the present invention can provide the high-quality adipic acid. The high-quality adipic acid obtained by the present invention is useful as intermediate raw materials for materials in various fields such as automobile components and electric components, and has industrial applicability.

REFERENCE SIGNS LIST

1 . . . reactor
2 . . . separator
3, 4, 5 . . . distillation column
6, 7 . . . raw material feed pipe
8, 10, 11, 12, 14, 15, 16 . . . pipe
9, 13 . . . return pipe
17 . . . purified product withdrawing pipe

The invention claimed is:

1. A purified cyclohexanol composition, comprising:
cyclohexanol;
methylcyclopentanol in a concentration of 10 to 1000 ppm by weight; and
cyclohexylcyclohexene isomer in a concentration of 15 to 344 ppm by weight.

2. A method for producing cyclohexanol comprising:
Step 1 of producing a solution (I) containing cyclohexanol, methylcyclopentanol, and water by a hydration reaction of cyclohexene;
Step 2 of separating the solution (I) into a water phase and an oil phase;
Step 3 of obtaining a partially purified cyclohexanol composition comprising cyclohexanol and methylcyclopentanol from the oil phase; and
Step 4 of separating and removing methylcyclopentanol in the partially purified cyclohexanol composition so as to obtain a purified cyclohexanol composition comprising cyclohexanol, methylcyclopentanol in a concentration of 10 to 1000 ppm by weight, and cyclohexylcyclohexene isomer in a concentration of 15 to 344 ppm by weight.

3. The method for producing cyclohexanol according to claim 2, wherein, in the Step 3,
a distillation column is used as an apparatus obtaining the partially purified cyclohexanol composition, and
the partially purified cyclohexanol composition is withdrawn from a middle part of the distillation column.

4. The method for producing cyclohexanol according to claim 2 or 3, wherein, in the Step 4,
a distillation column is used as an apparatus separating and removing methylcyclopentanol;
the partially purified cyclohexanol composition introduced into the distillation column contains 95 to 99.8% by weight of cyclohexanol and 1500 to 20000 ppm by weight of methylcyclopentanol; and temperatures of second to fifth plates from a top of the distillation column are controlled to 144 to 154° C. (700 mmHg).

5. A method for producing adipic acid, comprising a step of oxidizing a purified cyclohexanol composition, comprising cyclohexanol, methylcyclopentanol in a concentration of 10 to 1000 ppm by weight, and cyclohexylcyclohexene isomer in a concentration of 15 to 344 ppm by weight by nitric acid.

6. A purified cyclohexanol composition, consisting essentially of:
cyclohexanol;
methylcyclopentanol in a concentration of 10 to 1000 ppm by weight; and
cyclohexylcyclohexene isomer in a concentration of 15 to 344 ppm by weight.

7. A purified cyclohexanol composition, consisting of:
cyclohexanol;
methylcyclopentanol in a concentration of 10 to 1000 ppm by weight; and
cyclohexylcyclohexene isomer in a concentration of 15 to 344 ppm by weight.

8. The purified cyclohexanol composition of claim 1, wherein the cyclohexylcyclohexene isomer is in a concentration of 15 to 300 ppm by weight.

9. The purified cyclohexanol composition of claim 6, wherein the cyclohexylcyclohexene isomer is in a concentration of 15 to 300 ppm by weight.

10. The purified cyclohexanol composition of claim 7, wherein the cyclohexylcyclohexene isomer is in a concentration of 15 to 300 ppm by weight.

11. The purified cyclohexanol composition of claim 1, further comprising 1 ppm by weight or less of pentanol.

* * * * *